(12) United States Patent
Tiedje (10) Patent No.: US 8,910,632 B2
(45) Date of Patent: Dec. 16, 2014

(54) ENERGY TRIGGER (75) Inventor: Mikael Tiedje, Hisings Backa (SE)

(73) Assignee: Breas Medical, AB, Gothenburg (SE)

( * ) Notice: Subject to any disclaimer, the term of this patent is extended or adjusted under 35 U.S.C. 154(b) by 1152 days.

(21) Appl. No.: 11/570,943

(22) PCT Filed: Jun. 27, 2005

(86) PCT No.: PCT/EP2005/006881
§ 371 (c)(1),
(2), (4) Date: Dec. 19, 2006

(87) PCT Pub. No.: WO2006/005433
PCT Pub. Date: Jan. 19, 2006

(65) Prior Publication Data
US 2008/0283061 A1 Nov. 20, 2008

Related U.S. Application Data (60) Provisional application No. 60/610,137, filed on Sep. 15, 2004.

(30) Foreign Application Priority Data

Jul. 8, 2004 (SE) .................................... 0401810

(51) Int. Cl.
*A61M 16/00* (2006.01)

(52) U.S. Cl.
CPC ... *A61M 16/0051* (2013.01); *A61M 2205/3561* (2013.01); *A61M 2230/50* (2013.01); *A61M 2016/0036* (2013.01); *A61M 2205/3375* (2013.01); *A61M 2205/50* (2013.01); *A61M 2230/205* (2013.01); *A61M 2230/18* (2013.01); *A61M 2230/30* (2013.01); *A61M 16/0069* (2014.02); *A61M 2230/60* (2013.01); *A61M 2230/04* (2013.01); *A61M 2230/432* (2013.01); *A61M 2016/0027* (2013.01); *A61M 2230/435* (2013.01); *A61M 2230/10* (2013.01)
USPC ............. 128/204.23; 128/204.18; 128/204.21

(58) Field of Classification Search
USPC ............. 128/204.18, 204.21, 204.23, 202.27, 128/202.22
See application file for complete search history.

(56) References Cited

U.S. PATENT DOCUMENTS

| | | | | |
|---|---|---|---|---|
| 5,458,137 A | * | 10/1995 | Axe et al. ................. | 128/204.23 |
| 5,513,631 A | * | 5/1996 | McWilliams ............. | 128/204.23 |
| 5,660,171 A | | 8/1997 | Kimm et al. | |
| 6,484,719 B1 | * | 11/2002 | Berthon-Jones ......... | 128/204.23 |
| 6,532,960 B1 | * | 3/2003 | Yurko ....................... | 128/204.26 |
| 6,546,930 B1 | | 4/2003 | Emerson et al. | |
| 6,581,595 B1 | | 6/2003 | Murdock et al. | |
| 6,739,335 B1 | | 5/2004 | Rapport et al. | |
| 2003/0000528 A1 | | 1/2003 | Eklund et al. | |

FOREIGN PATENT DOCUMENTS

| | | |
|---|---|---|
| EP | 0 722 747 A | 7/1996 |
| NL | 1 001 423 C1 | 4/1997 |
| NL | 1001423 C1 | 4/1997 |

(Continued)

*Primary Examiner* — Patricia Bianco
*Assistant Examiner* — Keri J Nelson
(74) *Attorney, Agent, or Firm* — Alan Taboada; Moser Taboada (57) ABSTRACT

A method and apparatus for facilitating breathing using a mechanical breathing gas ventilator is presented. The patient effort is deduced from a measured flow signal and analyzed with respect to the energy in the breathing system comprising the mechanical ventilator and the patient. When a predetermined energy threshold has been reached the ventilator responds to the breathing pattern change.

12 Claims, 5 Drawing Sheets

(56) References Cited

FOREIGN PATENT DOCUMENTS

| WO | 94/23780 A | 10/1994 |
| WO | WO 2004/012597 A1 | 2/2004 |
| WO | 2005/011469 A | 2/2005 |

* cited by examiner

ENERGY TRIGGER

FIELD OF THE INVENTION

The present invention relates to the measurement and control of breathing gas administration into humans, and more specifically, the invention relates to a system for rapid response to changes of patient effort during ventilation of breathing gas.

BACKGROUND OF THE INVENTION

Patients suffering from different forms of breathing disorders can be subject to several types of treatments depending on the illness or disorder present. Such treatments include surgical procedures, pharmacologic therapy, and non-invasive mechanical techniques. Surgical techniques to remedy breathing disorders constitute a considerable risk for the patient and can lead to permanent injury or even mortality. Pharmacologic therapy has in general proved disappointing with respect to treating certain breathing disorders, e.g. sleep apnea. It is therefore of Interest to find other treatments, preferably non-invasive techniques.

A mechanical ventilator represents a non-invasive technique for treatment of certain breathing disorders such as ventilatory failure, hypoventilation, and periodic breathing during sleep and awake and in sleep apnea that occurs exclusively during sleep. Ventilatory failure includes all forms of insufficient ventilation with respect to metabolic need whether occurring during wake or periods of sleep. Hypoventilation and periodic breathing, in its most frequently occurring form referred to as Cheyne-Stokes ventilation, may occur periodically or constantly during wake or sleep. Conditions associated with hypoventilation, in particular nocturnal hypoventilation include e.g. central nervous system disorders such as stroke, muscular dystrophies, certain congenital conditions, advanced chronic obstructive pulmonary disease (COPD), etc. Cheyne-Stokes ventilation or various forms of central apnea are commonly associated with cardiac and circulatory disorders, in particular cardiac failure.

Ventilatory failure is a potentially life threatening condition. The general comorbidity in patients with failing ventilation is considerable. The condition is highly disabling in terms of reduced physical capacity, cognitive dysfunction in severe cases and poor quality of life. Patients with ventilatory failure therefore experience significant daytime symptoms but in addition, the majority of these cases experience a general worsening of their condition during state changes such as sleep. The phenomenon of disordered breathing during sleep, whether occurring as a consequence of ventilatory failure or as a component of sleep apnea in accordance with the description above causes sleep fragmentation. Daytime complications include sleepiness and cognitive dysfunction. Severe sleep disordered breathing occurring in other comorbid conditions like obesity, neuromuscular disease, post polio myelitis states, scoliosis or heart failure may be associated with considerable worsening of hypoventilation and compromised blood gas balance. Sleep apnea has been associated with cardiovascular complications including coronary heart disease, myocardial infarction, stroke, arterial hypertension, thrombosis, and cardiac arrhythmia. It is therefore of both immediate and long-term interest to reduce the exposure to sleep disordered breathing.

Recent advancement in mechanical non-invasive ventilator techniques includes administration of continuous positive airway pressure (CPAP) in different forms of sleep disordered breathing. During CPAP administration an elevated airway pressure is maintained throughout the breathing phase during a period coinciding with sleep. In sleep apnea this procedure may provide appropriate stabilization of the upper airway thereby preventing collapse. This, so called mono-level CPAP therapy, provides an almost identical pressure during inhalation and exhalation. Not only may CPAP be uncomfortable for the patient due to a sensed increased work of breathing during ventilation, specifically expiration. Some forms of apnea, mainly including those of central origin, and most forms of hypoventilation are only poorly controlled by CPAP. A more recently developed bi-level CPAP system administers different pressure levels during inhalation and exhalation. Bi-level CPAP provides increased comfort for most patients and not infrequently, an improved clinical response. Bi-level CPAP provides two pressure levels, inspiratory Positive Airway Pressure (IPAP) and Expiratory Positive Airway Pressure (EPAP). IPAP is administered during the inhalation phase while EPAP is given during the exhalation phase.

In ventilation treatment it is crucial that the inspiratory and expiratory phases synchronize with the patient efforts. A system that does not comply with patient efforts, creates an air trapping situation and increase discomfort for the patient as well as considerably increasing the possibility of anxiety for the patient.

Several different systems have been developed to make mechanical ventilators operate in accordance with patient rhythms. One key component in such systems is the ability to sense the patient rhythm or breathing phases. The early systems used pressure sensing devices to detect the pressure drop when patient tried to inhale. These systems however led to that the patient had to make a higher effort due to that the breathing tubing had to be depressurized before the trigger detection could be made, leaving the patient with a high effort level.

Succeeding the pressure systems was flow based systems which was based on a flow sensing mechanism. This was done by sensing the flow of gas entering and leaving the patient. There have been a number of methods of measuring the instantaneous and average gas flow described in literature to calculate the inspiratory and expiratory triggering points. One of the major problems in flow sensor mechanisms is that the system has to calculate the actual leakage from mask, mouth, and other leakages in the breathing circuits, that can lead to machine induced inspiratory triggering problems and missed inspiratory trigger. If this occurs it will result in that the ventilator is not responding to patient inspiratory and expiratory phases correctly and a high discomfort for the patient.

SUMMARY OF THE INVENTION

It is an object of the present invention to provide a system that remedies the above mentioned problems and provide an improved breathing gas ventilator solution for use in conjunction with ventilatory disorders, such as for instance as a bi-level continuous positive airway pressure (CPAP) method.

By measuring the actual patient effort to detect an inspiratory trigger the dependency of calculating the gas flow leakage will be of no importance. When the patient inhales, the effort made by the patient is equal to the amount of gas withdrawn from the breathing tube, if the leakage during inhalation is constant. Since the time from inhalation start to the triggering point lies in the region of 50-100 msec the leakage can be considered as constant.

The patient effort can then be calculated as the kinetic energy term in Bernoulli's equation for fluid medias. By measuring the kinetic energy which is proportional to the patient effort the actual work for the inspiration trigger can be calculated and presented as well. The method can also be used in weaning processes and in exercising patients with reduced breathing capacity.

In a preferred embodiment of the present invention a mechanical ventilator apparatus for use in delivering of breathing gas to humans is provided, the ventilator comprises:
a ventilator arrangement;
a processing unit; and
input means for obtaining sensor signals Indicative of at least breathing gas flow;
wherein the processing unit is arranged to analyze the flow signals with respect to energy content, trigger a response if the energy content reaches a trigger level, and regulating a supply of breathing gas in accordance with the reached trigger level.

The apparatus may be arranged so that the processing unit is arranged to apply the flow curve to a derivative procedure deriving the energy content and compare an output from the derivative procedure with at least one predetermined trigger level. The derivative may be indicative of the inhalation start phase or exhalation phase.

In another aspect of the present invention, a method for facilitating breathing in connection with a mechanical ventilator arrangement is provided, the method comprising the steps of:
measuring a breathing gas flow;
processing the breathing gas flow for energy content;
determining if the energy content has reached a trigger level; and
responding to the reached trigger level by changing control signals for the mechanical ventilator, the control signals controls the supply of breathing gas.

The processing unit may be applying the flow curve to a derivative procedure in order to deduce the energy content and comparing an output from the derivative procedure with at least one predetermined trigger level. The processing unit may be further arranged to obtain a pressure signal and using this pressure signal in the process of determining the energy content.

Yet another preferred embodiment of the present invention, a system for facilitating breathing when using a mechanical ventilator arrangement is provided, comprising:
at least one sensing means for measuring flow of breathing gas to a patient;
a breathing gas tubing and breathing gas distribution means;
a mechanical ventilator apparatus; and
a processing unit;
wherein the processing unit is arranged to process data obtained from the sensing means for measuring flow of breathing gas, to determine when a trigger level is reached by data indicative of energy of breathing obtained from the flow measurements, and respond to the reached trigger level by changing control signals controlling a supply of breathing gas in the mechanical ventilator apparatus.

In the system the processing unit may be arranged to apply the flow curve to a derivative procedure in order to deduce the energy content and compare an output from the derivative procedure with at least one predetermined trigger level. The processing unit may be further arranged to obtain a pressure signal and using this pressure signal in the process of determining the energy content.

Another embodiment of the present invention, a computer program for controlling a mechanical ventilator apparatus is provided, wherein the program operate on signals obtained from at least one sensing means for measuring flow of breathing gas to a patient, the program determines if a trigger level has been reached by data indicative of energy of breathing obtained from the flow measurement, and the program transmits control signals to a mechanical ventilator in response if the trigger level has been reached in order to control the supply of breathing gas.

The computer program may further be arranged to apply the flow curve to a derivative procedure deducing the energy content and compare an output from the derivative procedure with at least one predetermined trigger level. The derivative procedure may be indicative of the inhalation rise phase or the exhalation fall phase. The computer program mat be further arranged to obtain a pressure signal and using this pressure signal in the process of determining the energy content.

BRIEF DESCRIPTION OF THE DRAWINGS

In the following the invention will be described in a non-limiting way and in more detail with reference to exemplary embodiments illustrated in the enclosed drawings, in which.

DETAILED DESCRIPTION OF THE INVENTION

Figure 1:
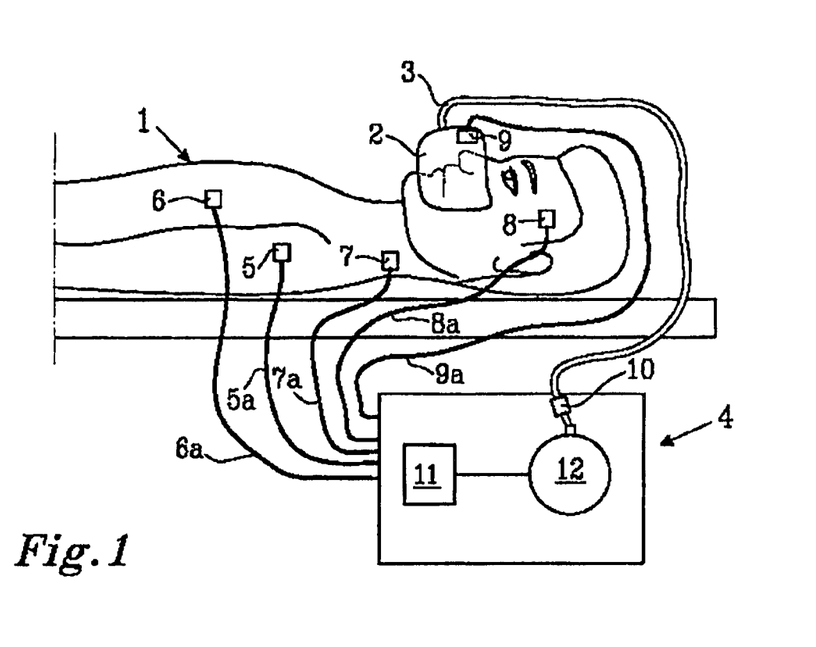
FIG. 1 is a schematic depiction of a ventilatory system according to the present invention.

In FIG. 1 a schematic mechanical ventilation system used for the treatment of hypoventilation disorders is depicted. A ventilation system comprise a mechanical ventilator 4 supplying pressurized breathing gas, tubing 3 for guiding breathing gas to the patient 1, a breathing mask 2 or similar for administrating the breathing gas to the patient 1, sensing means 5, 6, 7, 8, 9 and 10 for determining the physiological status of the patient 1. The number of sensors connected to the mechanical ventilator may be one or more; however, in a preferred embodiment of the present invention at least one sensor is necessary: a breathing gas flow measurement which may be located essentially anywhere along the breathing gas tubing or in the mask. A mechanical ventilator 4 is supplying breathing gas for instance as a positive airway pressure via a tubing 3 and through a mask 2 to a patient 1. The mask 2 can be a face mask 2 covering both the mouth and nose or a nasal mask covering only the nose or nostrils depending on the patients needs. It can also be a hood covering the complete head or body of the patient.

The breathing gas may be of any suitable gas composition for breathing purposes as understood by the person skilled in the art, the composition may depend on the physiological status of the patient.

The pressure or flow from the ventilator 4 is controlled by a processing unit 11 as shown in FIG. 1. The processing unit 11 may involve a computer program that measures one or several input parameters 5, 6, 7, 8, 9, and 10 obtained from the patient 1 describing the physiological status of the patient and pressure/flow data indicative of breathing gas system configuration and status. Data indicative of patient status is obtained using sensors 5, 6, 7, 8, 9, and 10 connected to the patient and transferred to the processing unit 11 via connection means 5a, 6a, 7a, 8a, and 9a (connection means for sensor 10 is not depicted in FIG. 1 since the sensor may be placed at several different locations, such as inside the ventilator apparatus). These input parameters may be for instance flow or pressure signals, data obtained from EEG, EMG, EOG, and ECG measurements, $O_2$ and/or $CO_2$ measurements in relation to the patient, body temperature, blood pressure, SpO2 (oxygen saturation), eye movements, and sound measurements. It should be understood that the invention is not limited to the above mentioned input parameters but other input parameters may be used. In FIG. 1 not all sensors 5, 6, 7, 8, 9, and 10 and sensor connection means 5a, 6a, 7a, 8a, and 9a are depicted, only a subset is shown in order to illustrate a schematical view of the system and the depicted locations are only given as examples and are in no way limiting to the invention, e.g. the flow signal may be measured at either the mask location or close to the mechanical ventilator or at both locations in order to deduce a differential signal if this is required.

The flow sensor 10 may be located at several different positions, e.g. in the breathing air tubing 3 at any suitable position, such as close to the mechanical ventilator apparatus (or even within the ventilator housing) or in the vicinity of the mask.

In a preferred embodiment of the present invention only the flow is used in the process and thus is the only parameter measured. However, in another preferred embodiment of the present invention also the pressure value is used in the process together with the flow data and thus also a pressure measurement is used as well. However it should be appreciated by the person skilled in the art that more signals then the flow and pressure signals may be used in the process depending on the algorithm used for determining an energy content of the obtained signals (as will be discussed in more detail below).

Figure 2:
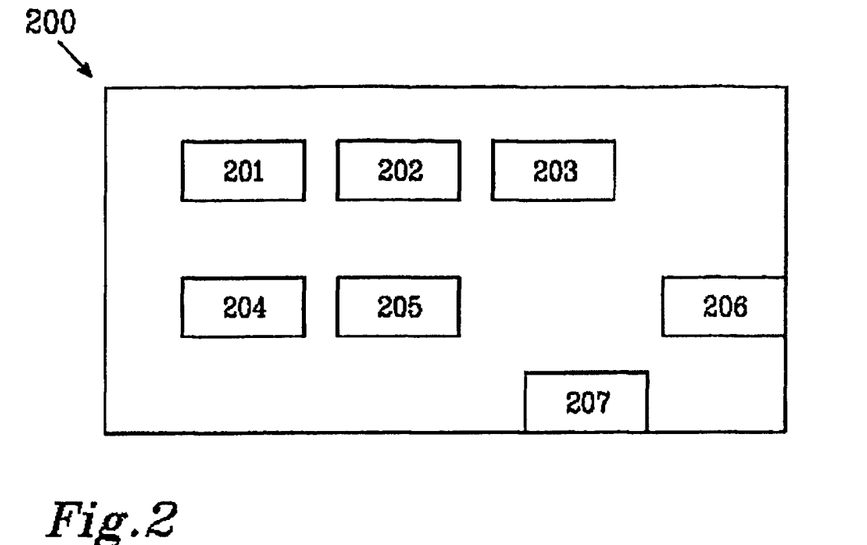
FIG. 2 is a schematic block diagram of a ventilator apparatus according to the present invention.

The input data is supplied to a processing unit 11 comprising at least computational means 201. The computational or processing means 201 analyses the measured data, preferably data from the flow measurement, according to an appropriate algorithm or algorithms (to be discussed in detail below) in order to determine an appropriate response and send control signal or signals to a mechanical ventilator unit 12. This mechanical ventilator unit 12 may be a fan 12 arranged to deliver appropriate amounts of breathing gas at specified and controlled pressure levels.

The mechanical ventilator device 4 there may also comprise a data storage unit 202 for post analysis and inspection and also a connection for an external non-volatile memory device, like for instance a memory device using a USB connection, an external hard drive, a floppy disk, a CD-ROM writer, a DVD writer, a Memorystick, a Compact Flash memory, a Secure Digital memory, an xD-Picture memory card, or a Smart Media memory card. These are only given as examples, and are not limiting for the invention, many more external memory devices may be used in the invention as appreciated by the person skilled in the art.

The mechanical ventilator may also have input means (not shown) for manually setting control parameters and other parameters necessary for the operation of the device.

Through a communication means 207 it is possible to communicate with the device 4 to and from an external computational device for retrieving data and results for later analysis and/or inspection. The communication means can be of a serial type like for instance according to the standards RS232, RS485, USB, Ethernet, or Firewire, or of a parallel type like for instance according to the standards Centronics, ISA, PCI, or GPIB/HPIB. It may also be any wireless system of the standards in the IEEE 802.11 series, HiperLAN, Bluetooth, IR, GSM, GPRS, or UMTS, or any other appropriate fixed or wireless communication system capable of transmitting measurement data. It can also be of any proprietary non-standardized communication formats, whether it is wireless or wired.

The ventilator device 4 may also have display means (not shown) for displaying measured data and obtained response parameters for use by a physician, other medical personnel, or the patient. The display means may be of any normal type as appreciated by a person skilled in the art. The data is displayed with such a high rate that a real time feedback is provided to a person monitoring the ventilator characteristics and function for immediate feedback and control.

In a preferred embodiment of the present invention, the system responds to patient breathing changes by measuring the breathing effort the patient puts into the system. This measurement may be accomplished by calculating the kinetic energy term in Bernoulli's theorem for an ideal gas at a measuring point in the breathing gas supply system comprising the mechanical ventilator 4, the tube 3, and the mask 2 (or even inside the patient 1).

Figure 3:
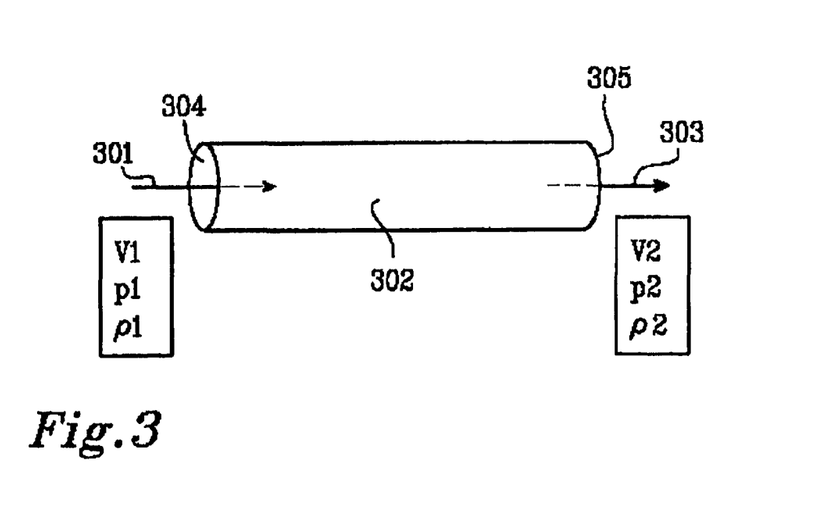
FIG. 3 is a schematic diagram of air flow tubing.

The basis behind the process may be illustrated by the known Bernoullis theorem for an ideal gas flowing at speed V:

$$p + \tfrac{1}{2}\rho V^2 \rho g h = \text{constant} \qquad \text{Eq. 1}$$

where p is the pressure, ρ is the density of the gas, g is the acceleration of gravity, and h is the height. Referring to a situation as depicted in FIG. 3, wherein a flow of gas from a ventilator device enters the breathing gas tubing 3 and exits in the mask 2 located close to the patient 1, the above equation may then be rewritten due to the fact that according to Bernoullis theorem the equation must be equal at the two ends of the tubing 3. This gives the equality:

$$p_1 + \tfrac{1}{2}\rho_1 V_1^2 + \rho_1 g h = p_2 + \tfrac{1}{2}\rho_2 V_2^2 + \rho_2 g h \qquad \text{Eq. 2}$$

Returning now to the interpretation of Eq. 1, the first term (p) is a so called "work" term, the second term ($\tfrac{1}{2} \rho V^2$) is a so called "kinetic" energy term, and the final term (ρg h) is a so called "potential" energy term. When a patient inhales, the kinetic energy term in the system is increased:

$$p_2 + \tfrac{1}{2}\rho_2 V_2^2 + \tfrac{1}{2}\Delta\rho_2 \Delta V_2^2 + \rho_2 g h \qquad \text{Eq. 3}$$

Figure 4:
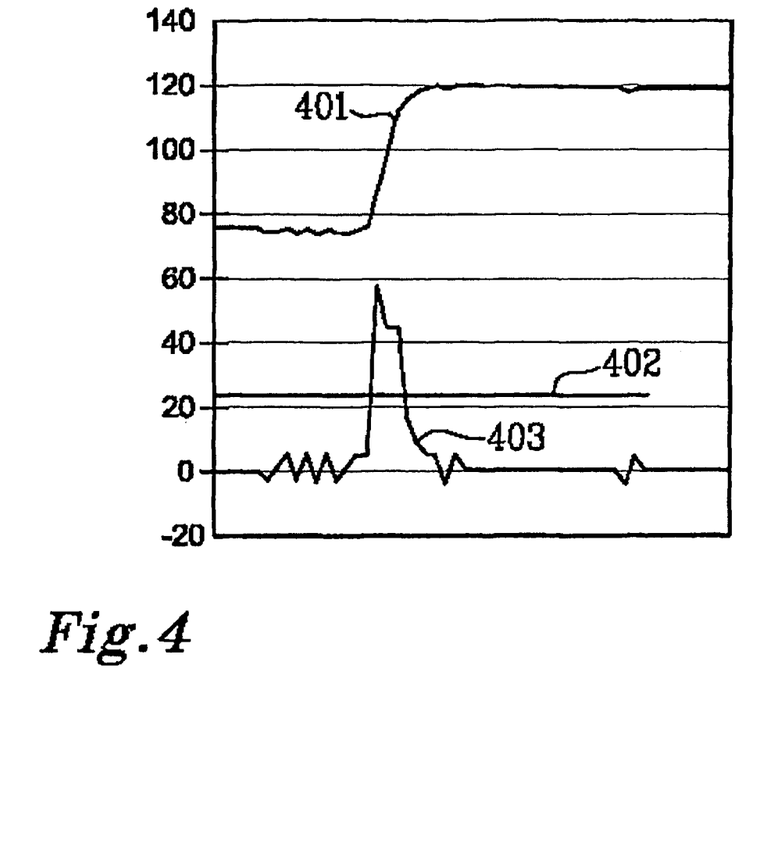
FIG. 4 is a schematical example of a measured flow curve with corresponding energy curve according to the present invention.

The third term in Eq. 3 ($\tfrac{1}{2} \Delta\rho_1 \Delta V_2^1$) is the patient "added energy" term. This change of energy output proportional to the effort by the patient may be measured and calculated at the energy input 301 via, for example, a derivative procedure. In FIG. 4 a typical example of a flow measurement 401 from a mechanical ventilator system is shown. In the illustration the flow curve derivative 402 indicative of the energy and a trigger level 403 are also depicted. As can be seen in FIG. 4 during the rise of the flow curve the energy term increases significantly and when the energy term pass the threshold level the system is triggered to respond to the change of effort, this may be called Inspiratory triggering. In such a way it is possible for the system to respond quickly and reduce the effort for the patient, while at the same time Increasing the well being for the patient and lowering the risk of causing the patient anxiety.

In a similar fashion the system may respond to the exhalation phase of the breathing cycle, which may be called Expiratory triggering (some times called expiration termination criteria). However, the flow curve will of course be opposite to the inhalation phase and correspondingly the energy term will also be opposite. This may be seen in FIG. 5, wherein both inhalation and exhalation phases of the breathing cycle are demonstrated.

Figure 5:
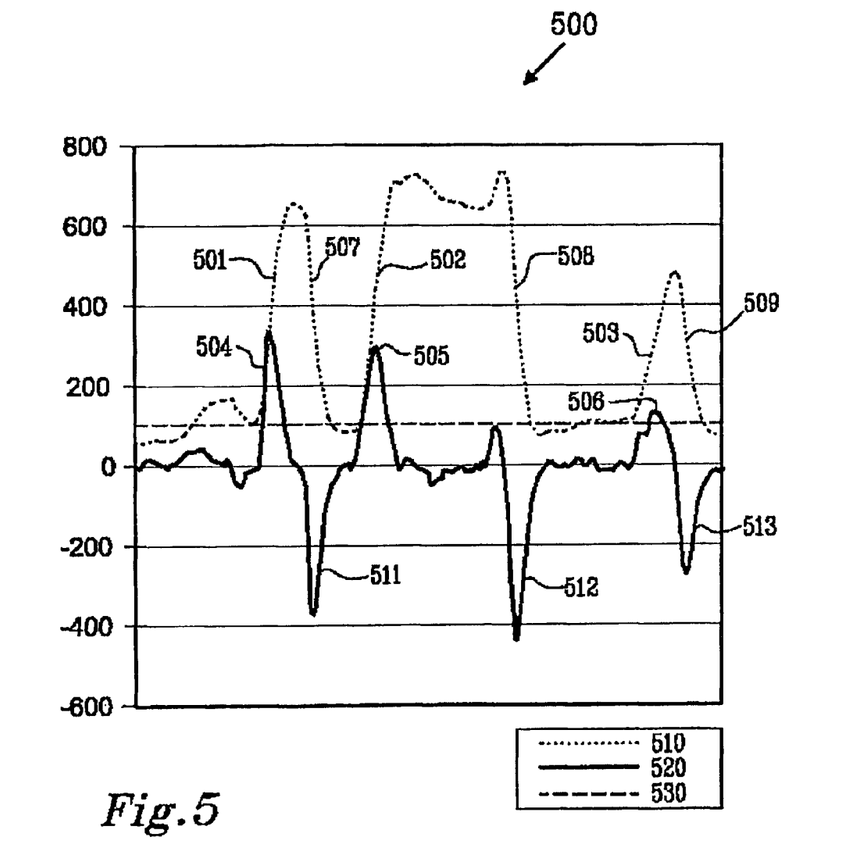
FIG. 5 is another schematic example of flow curve and corresponding energy curve according to the present invention.

In FIG. 5 a flow measurement curve 510, a processed energy curve 520, and a trigger level 530 is depicted. The rise of the inhalation phases are marked with 501, 502, and 503 while corresponding energy terms are marked 504, 505, and 506. In a similar fashion exhalation phases are marked with 507, 508, and 509 with the corresponding energy terms marked as 511, 512, and 513. As can be seen during the start of the inhalation phase 501, 502, and 503 a significant increase of the energy term 504, 505, and 506 is detected and in FIG. 5 a trigger level 530 is set in order to illustrate that at some point the energy curve 520 will reach this trigger level 530. When an inspiration trigger 504, 505, and 506 is released the ventilator may respond by increasing the pressure in the distribution system 2 and 3. If an expiration trigger 511, 512, and 513 is released the ventilator respond may respond by decreasing the pressure in the distribution system 2 and 3.

Care must of course be taken in setting the threshold for where a response should be triggered in order to ensure that no false triggers are given. For the same purpose care should also be taken in how sampled data is processed, e.g. filtering or averaging functions, to reduce noise and other external or internal signal disturbances. It should be appreciated by the person skilled in the art that many types of signal processing means may be utilized in order to improve signal quality as may be found in the standard tools of the trade, such as low-pass filtering techniques or other filtering solutions, different averaging solutions, and other more complex signal processing steps such as fourier analysis. These different "noise" reducing solutions may be implemented either as hardware solutions in the signal path or as software solutions after sampling the signals. The software solutions may be implemented in the processing unit of the ventilator apparatus of as a separate signal sampling unit (not shown) preprocessing data.

The ventilator apparatus may have hardware or software means (not shown) for adjusting trigger levels for both inhalation and exhalation phases separately.

Figure 6:
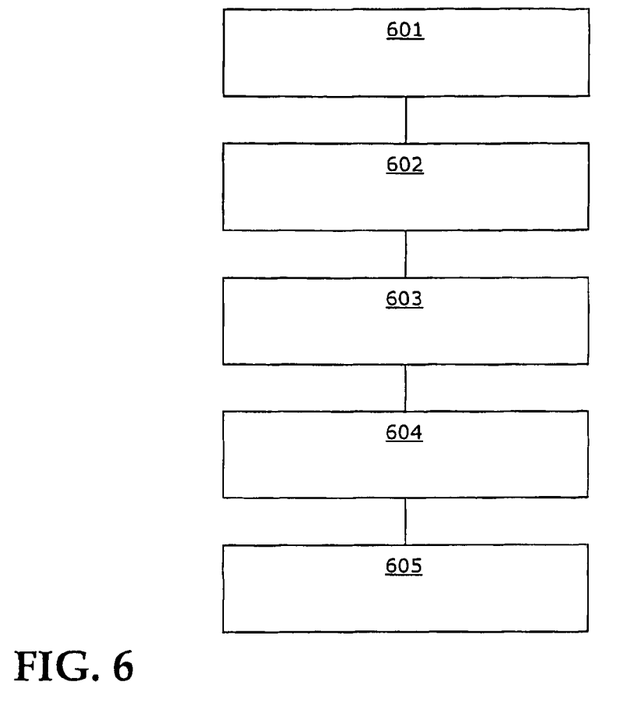
FIG. 6 is a schematic illustration of a method according to the present invention.

A method for using the above mentioned procedure Is illustrated in FIG. 6. The method comprises the following steps:
   Periodically acquiring 601 sampled input parameters 5, 6, 7, 8, 9, and 10 indicative of patient physiological status.
   measuring a breathing gas flow sensor signal 602;
   deriving an energy term from said flow sensor signal using a derivate procedure 603;
   detecting if the energy term pass through a predetermined threshold level 604; and
   triggering a response from the ventilator upon such a threshold detection 605 be changing control signals for controlling the breathing gas supply in the ventilator apparatus.

There are many types of ventilation modes where the above described method and apparatus may find its application including but not limited to:
   1. Continuous positive airway pressure (CPAP),
   2. Synchronized Intermittent mandatory ventilation (SIMV),
   3. Assist control mechanical ventilation (ACMV),
   4. Pressure control ventilation (PCV),
   5. Pressure support ventilation (PSV),
   6. Proportional assist ventilation (PAV), and
   7. Volume assured pressure support (VAPS)

The system may also be used for exercising patients or healthy persons in order to increase their lung capacity which has been reduced for some reason, e.g. after some surgical procedure, accident, medical illness. By exercising, it is possible to reduce risks for patients with reduced breathing capacities. It may also be possible to use the method in weaning processes wherein patients connected to a respirator train with a system according to the present invention in order to remove the need for the respirator. This is a gradual process where the patient's diaphragm is trained until the patient is strong enough to breathe without the help from a respirator.

These kinds of methods and devices are often used for treating disturbed breathing during for instance sleep either in the home or in a clinical environment. The methods and devices described above within the scope of the invention may also be used for treatment of many other different forms of ventilatory failure events or hypoventilation events, and treatment may be done both at home and in the clinical environment. Examples of groups of breathing disorders include, but are not limited to, breathing disorders during sleep, obstructive lung diseases (COPD), neuromuscular disorders, neurological disorders, chest wall disorders, and more.

The above mentioned and described embodiments are only given as examples and should not be limiting to the present invention. Other solutions, uses, objectives, and functions within the scope of the invention as claimed in the below described patent claims should be apparent for the person skilled in the art.

The invention claimed is:

1. A mechanical ventilator apparatus for supplying breathing gas to humans, the ventilator comprising:
   a ventilator arrangement; and
   a processing unit configured to obtain flow signals from sensors indicative of at least breathing gas flow;
   wherein said processing unit is arranged to analyze said flow signals with respect to kinetic energy content relating to a breathing effort of a patient by applying said flow signals to a derivative procedure in order to deduce said kinetic energy content via a calculation of $\frac{1}{2}\rho V^2$, where $\rho$ is a density of breathing gas and V is a speed of a breathing flow gas, and said derivative procedure further comparing an output from said derivative procedure to at least one predetermined trigger level, to trigger a response if said kinetic energy content reaches said trigger level, and to trigger at least one of an inspiratory phase or an expiratory phase of a breathing cycle using a supply of said breathing gas according to said reached trigger level.

2. The apparatus according to claim 1, wherein said derivative output is indicative of the inhalation start phase.

3. The apparatus according to claim 1, wherein said derivative output is indicative of the exhalation start phase.

4. The apparatus according to claim 1, wherein said processing unit is further configured to receive a signal indicative of pressure, and to use said signal indicative of pressure in said analysis for kinetic energy content together with said signal indicative of breathing gas flow.

5. A method for facilitating breathing in connection with a mechanical ventilator arrangement, comprising the steps of:
   acquiring a breathing gas flow signal;
   processing said breathing gas flow signal for kinetic energy content by applying said breathing gas flow signal to a derivative procedure to deduce said kinetic energy content relating to a breathing effort of a patient, wherein the kinetic energy content is deduced via a calculation of $\frac{1}{2}\rho V^2$, where $\rho$ is a density of breathing gas and V is a speed of a breathing flow gas;
   determining if said kinetic energy content has reached at least one predetermined trigger level by comparing an output from said derivative procedure with said trigger level; and responding to said reached trigger level by changing control signals for said mechanical ventilator, wherein said control signals trigger at least one of an inspiratory phase or an expiratory phase of a breathing cycle using a supply of breathing gas.

6. The method according to claim 5, further comprising the steps of:
measuring a breathing gas pressure; and
using said pressure measurement in said processing for kinetic energy content.

7. A system for facilitating breathing when using a mechanical ventilator arrangement, comprising:
at least one sensing means for acquiring a flow signal indicative of at least flow of breathing gas to a patient;
a breathing gas tubing and breathing gas distribution means;
a mechanical ventilator apparatus; and
a processing unit;
wherein said processing unit is arranged to process flow data obtained from a breathing gas flow measurement using said sensing means, to determine kinetic energy content relating to a breathing effort of a patient from said flow data by applying said flow signal to a derivative procedure to deduce said kinetic energy content via a calculation of $\frac{1}{2}\rho V^2$, where $\rho$ is a density of breathing gas and V is a speed of a breathing flow gas, and said derivative procedure further comparing an output from said derivative procedure with at least one predetermined trigger level, to determine if said predetermined trigger level is reached from said comparison, and to output control signals to said mechanical ventilator apparatus to trigger at least one of an inspiratory phase or an expiratory phase of a breathing cycle using a supply of breathing gas.

8. The system according to claim 7, further comprising:
sensing means for measuring breathing gas pressure;
said processing unit being arranged to process data from both flow and pressure measurements in order to deduce kinetic energy content.

9. A computer readable medium having instructions stored thereon that, when executed, control a mechanical ventilator apparatus, to perform a method, comprising:
obtaining flow signals from at least one sensing means for measuring flow of breathing gas to a patient;
applying said flow signals to a derivative procedure to deduce a kinetic energy content relating to a breathing effort of a patient, wherein the kinetic energy content is deduced via a calculation of $\frac{1}{2}\rho V^2$, where $\rho$ is a density of breathing gas and V is a speed of a breathing flow gas;
comparing an output from said derivative procedure with at least one predetermined trigger level;
determining from said comparison if said predetermined trigger level has been reached; and
transmitting control signals to trigger at least one of an inspiratory phase or an expiratory phase of a breathing cycle using a supply of breathing gas to said mechanical ventilator if said predetermined trigger level has been reached.

10. The computer readable medium according to claim 9, wherein said output from said derivative procedure is indicative of the inhalation rise phase.

11. The computer readable medium according to claim 9, wherein said output from said derivative procedure is indicative of the exhalation fall phase.

12. The computer readable medium according to claim 9, further comprising using data obtained from measurement of breathing gas pressure together with flow measurements in determining said kinetic energy content.

\* \* \* \* \*